United States Patent
Uchida

(10) Patent No.: US 8,752,961 B2
(45) Date of Patent: Jun. 17, 2014

(54) FUNDUS PHOTOGRAPHING APPARATUS

(75) Inventor: Hiroki Uchida, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 110 days.

(21) Appl. No.: 12/783,324

(22) Filed: May 19, 2010

(65) Prior Publication Data

US 2010/0296056 A1 Nov. 25, 2010

(30) Foreign Application Priority Data

May 22, 2009 (JP) ................................ 2009-124349

(51) Int. Cl.
*A61B 3/14* (2006.01)
*A61B 3/00* (2006.01)
*G06K 9/00* (2006.01)

(52) U.S. Cl.
USPC ............................ 351/206; 351/200; 382/117

(58) Field of Classification Search
USPC ................. 351/200, 203, 205, 206, 222, 243; 382/128, 131, 117; 348/78, 64, 73, 68
See application file for complete search history.

(56) References Cited

U.S. PATENT DOCUMENTS

| 6,104,828 A * | 8/2000 | Shioiri | 382/128 |
| 6,224,212 B1 * | 5/2001 | Noda et al. | 351/206 |
| 6,636,696 B2 * | 10/2003 | Saito | 396/18 |
| 6,755,526 B2 * | 6/2004 | Shibata | 351/206 |
| 2008/0316426 A1 * | 12/2008 | Shibata et al. | 351/206 |
| 2009/0136100 A1 * | 5/2009 | Shinohara | 382/128 |
| 2009/0202113 A1 * | 8/2009 | Fujii et al. | 382/117 |

FOREIGN PATENT DOCUMENTS

JP 2007-252707 A 10/2007

* cited by examiner

*Primary Examiner* — Thomas K Pham
*Assistant Examiner* — Brandi Thomas
(74) *Attorney, Agent, or Firm* — Canon USA Inc IP Division

(57) ABSTRACT

A fundus photographing apparatus includes an imaging unit configured to capture a fundus image of an subject's eye via a photographing optical system, an imaging magnification output unit configured to output imaging magnification of the photographing optical system, a fixation target presenting unit configured to make the subject's eye to look firmly at a fixation target, a fixation target presenting position detection unit configured to detect a presenting position of the fixation target presenting unit, a matching area determination unit configured to determine an area for matching a fundus image based on the imaging magnification and the presenting position of the fixation target, and a correlation value calculation unit configured to calculate a correlation value between a plurality of fundus images captured by the imaging unit based on the matching area determined by the matching area determination unit.

19 Claims, 11 Drawing Sheets

FUNDUS PHOTOGRAPHING APPARATUS

BACKGROUND OF THE INVENTION

1. Field of the Invention

The present invention relates to a fundus photographing apparatus, such as a fundus camera, used in an opthalmological clinic.

2. Description of the Related Art

Conventionally, fundus photographing by a fundus camera has been widely used to perform screening in a medical check in a group or diagnose opthalmologic diseases. A photographed fundus image is generally recorded as digital data. The photographed data is stored in a mobile recording medium or a hard disk drive built in a personal computer (PC).

The conventional fundus photographing by a fundus camera includes fluorescent photographing performed by intravenously administering a fluorescent contrast agent into a subject, in addition to color photographing. However, with recent increase of the number of patients suffering from age-related macular degeneration (AMD), fundus auto-fluorescence (FAF) photographing draws attention as a new photographing method. Although the FAF photographing has been mounted on a laser scanning type optometry device in early days, the FAF photographing is beginning to be applied to a fundus camera in recent years.

The FAF photographing is different from the conventional fluorescent photographing, and is performed without intravenous injection of the fluorescent contrast agent into a subject. It has been known that lipofuscin, which is a fluorescent substance, is deposited on a retinal pigment epithelium of the AMD patient. The FAF photographing photographs fluorescence emitted by the lipofuscin, and finds out a lesion characteristic of the AMD.

However, the fluorescence emitted by lipofuscin on a fundus retina is extremely weak, and it is difficult for a conventional photographing film or a digital image sensor to obtain an FAF image which can be used for a clinical examination by only one photographing. Therefore, there is a method for executing FAF photographing a plurality of times and performing addition combination of the obtained plurality of FAF images to obtain an FAF image having a better image quality.

When a fundus photographing apparatus performs addition combination of a plurality of fundus images, slight position deviations may occur between each fundus image due to insufficient fixation or micro-motion of fixation of a subject. Accordingly, addition combination could not be performed preferably. Therefore, Japanese Patent Application Laid-Open No. 2007-252707 discusses that it is indispensable for the addition combination of fundus images to combine the images after adjusting position deviations occurring between the images.

As described above, since fluorescence on the fundus retina of the AMD patient is extremely weak, it is necessary to greatly increase a sensitivity of an image sensor when the FAF photographing is performed. However, an FAF image acquired by photographing with increased sensitivity includes a lot of noise components. Thus, a primary FAF image may be buried in the mass noise components.

A conventional method which extracts a characteristic high-frequency component from an image could misunderstand the noise component as a characteristic area, so that a position deviation may not be properly corrected. Further, searching a characteristic area from an entire image is processing including a heavy load in itself, and the processing needs much time for correcting the position deviations.

SUMMARY OF THE INVENTION

The present invention is directed to a fundus photographing apparatus capable of correcting a position deviation at high speed and with high accuracy by uniquely determining an area to be used for correcting the position deviation using photographing conditions at a time of fundus photographing.

According to an aspect of the present invention, a fundus photographing apparatus includes an imaging unit configured to capture a fundus image of an subject's eye via a photographing optical system, an imaging magnification output unit configured to output imaging magnification of the photographing optical system, a fixation target presenting unit configured to make the subject's eye to look firmly at a fixation target, a fixation target presenting position detection unit configured to detect a presenting position of the fixation target presenting unit, a matching area determination unit configured to determine an area for matching a fundus image based on the imaging magnification and the presenting position of the fixation target, and a correlation value calculation unit configured to calculate a correlation value between a plurality of fundus images captured by the imaging unit based on the matching area determined by the matching area determination unit.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention, and together with the description, serve to explain the principles of the invention.

DESCRIPTION OF THE EMBODIMENTS

Various exemplary embodiments, features, and aspects of the invention will be described in detail below with reference to the drawings.

Figure 1:
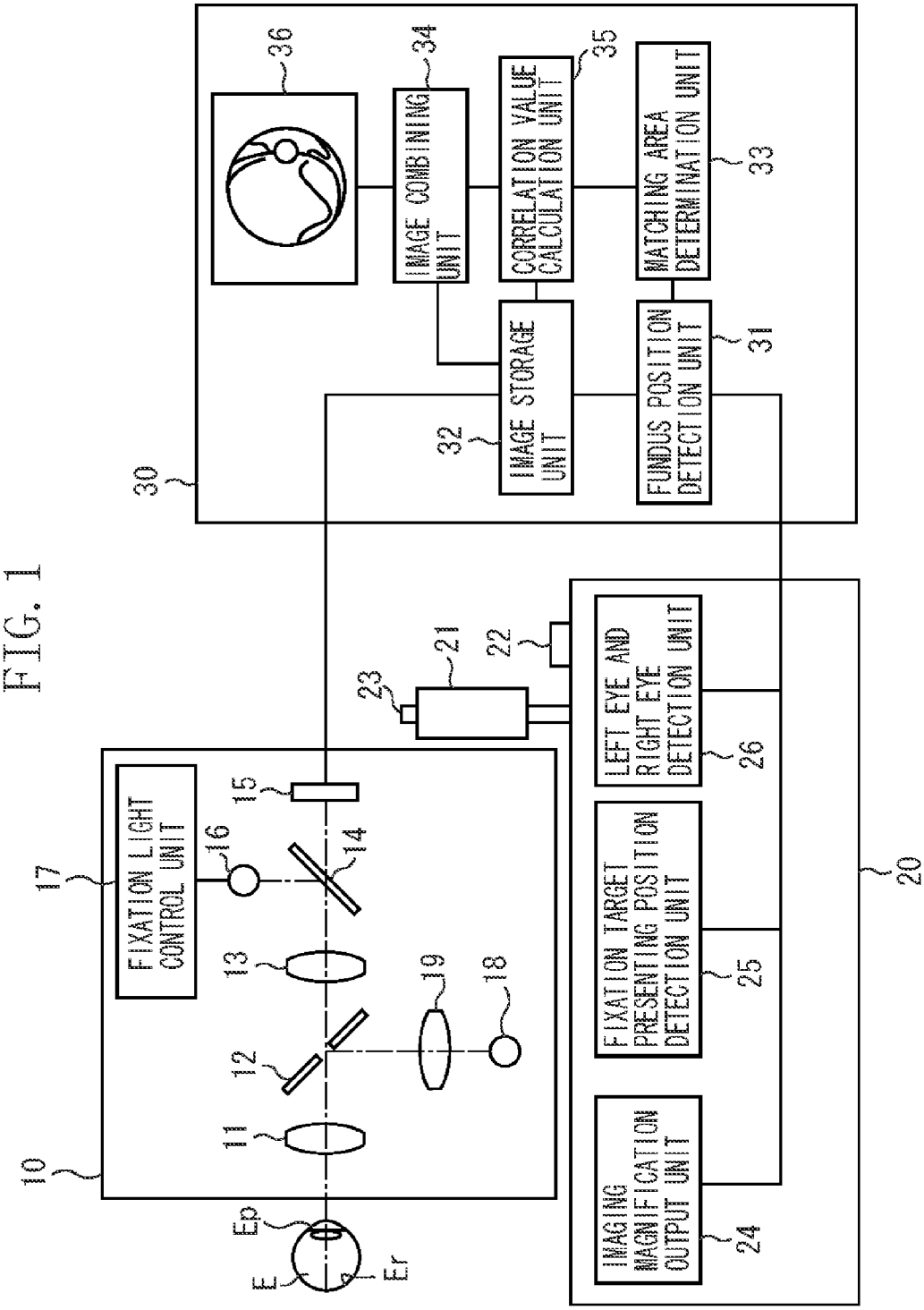
FIG. 1 is a configuration diagram illustrating a fundus photographing apparatus in an exemplary embodiment of the present invention.

FIG. 1 illustrates a configuration of a fundus photographing apparatus of the present exemplary embodiment. The fundus photographing apparatus includes a head unit 10 arranged in front of a subject's eye E, a stage unit 20 on which the head unit 10 is mounted, and an image processing unit 30 which is electrically connected to the head unit 10 and the stage unit 20.

In the head unit 10, an objective lens 11, a perforated mirror 12, a photographic lens 13, a flip-up mirror 14 which retreats from a photographing optical path at a time of photographing, and an image sensor 15 are arranged in front of a subject's eye E, so that a photographing optical system is configured. In the photographing optical system, light reflected from a fundus Er of the subject's eye E passes through the objective lens 11 and a hole of the perforated mirror 12, and forms an image on the image sensor 15 through the photographic lens 13.

Figure 2:
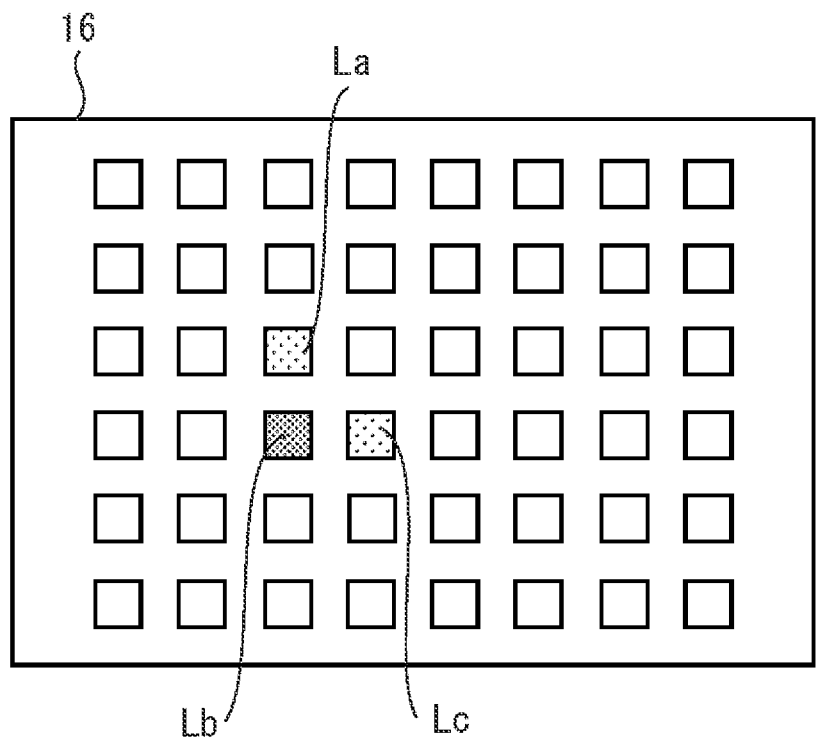
FIG. 2 illustrates a front view of a fixation light configured with a light emitting diode (LED) light source.

The head unit 10 includes a fixation light 16 arranged in an incidence direction of the flip-up mirror 14. FIG. 2 illustrates a front view of the fixation light 16. The fixation light 16 includes a plurality of LEDs arranged in a lattice shape. By lighting one LED, the fixation light 16 can guide a sight line of the subject's eye E to a direction of the LED lighting. The fixation light 16 is connected to a fixation light control unit 17, and can arbitrarily change a position to project a fixation target to the subject's eye E. The fixation light 16 is arranged at a position conjugated with the fundus Er, and can project the fixation target on the fundus Er of the subject's eye E through the flip-up mirror 14, the photographic lens 13, the perforated mirror 12, and the objective lens 11.

The head unit 10 further includes an illumination lens 19 and an illumination light source 18 which are arranged in an incidence direction of the perforated mirror 12, so that an illumination optical system is configured. In the illumination optical system, light emitted from the illumination light source 18 passes through the illumination lens 19, is reflected to a direction of the subject's eye E by the perforated mirror 12, and illuminates the fundus Er through the object lens 11.

The stage unit 20 includes an operation lever 21, a fixation light operation switch 22, and a photographing switch 23 on the operation lever 21. Further, the stage unit 20 internally includes an imaging magnification output unit 24, a fixation target presenting position detection unit 25, and a left eye and right eye detection unit 26.

Figure 3:
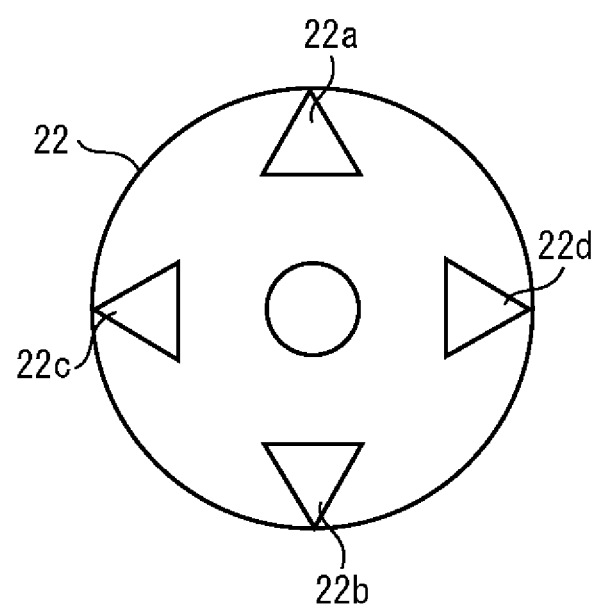
FIG. 3 illustrates a front view of an operation unit configured to change a presenting position of a fixation light.

The operation lever 21 enables photographing while switching a left eye and a right eye of a subject by operating the head unit 10. As illustrated in FIG. 3, the fixation light operation switch 22 includes an upward movement switch 22a, a downward movement switch 22b, a leftward movement switch 22c, and a rightward movement switch 22d. The fixation light operation switch 22 can move a presenting position of the fixation light 16 to upward, downward, leftward, and rightward via the fixation light control unit 17. In the stage unit 20, the imaging magnification output unit 24 outputs an imaging magnification of the photographing optical system. The fixation target presenting position detection unit 25 outputs a projection position of the fixation light 16. The left eye and right eye detection unit 26 determines whether the subject's eye E is a left eye or a right eye, from a position relationship between the stage unit 20 and the head unit 10.

A fundus position detection unit 31 in the image processing unit 30 is connected to each output from the imaging magnification output unit 24, the fixation target presenting position detection unit 25, and the left eye and right eye detection unit 26 in the stage unit 20. An output of the fundus position detection unit 31 is connected to an image storage unit 32.

An output from the image sensor 15 of the head unit 10 is also connected to the image storage unit 32. An output of the image storage unit 32 is connected to an image combining unit 34 and a correlation value calculation unit 35. An output of the image combining unit 34 is connected to an image display unit 36 and a matching area determination unit 33 via the correlation value calculation unit 35.

The image storage unit 32 can store and read fundus images photographed by the image sensor 15. The fundus position detection unit 31 can detect rough specific positions of an optic papillary portion, a medium and large blood vessel portion, and a macular portion in the photographed image of the subject's eye.

Based on position information of the specified optic papillary portion, medium and large blood vessel portion, and macular portion, the matching area determination unit 33 determines a matching area needed for adjusting a position. Further, the matching area determination unit 33 can calculate a correlation value between a plurality of fundus images stored in the image storage unit 32.

Based on the correlation value between the images calculated by the correlation value calculation unit 35, the image combining unit 34 can perform position adjustment and combination of the plurality of the fundus images stored in the image storage unit 32. The image display unit 36 displays the fundus image combined by the image combining unit 34.

Figure 4:
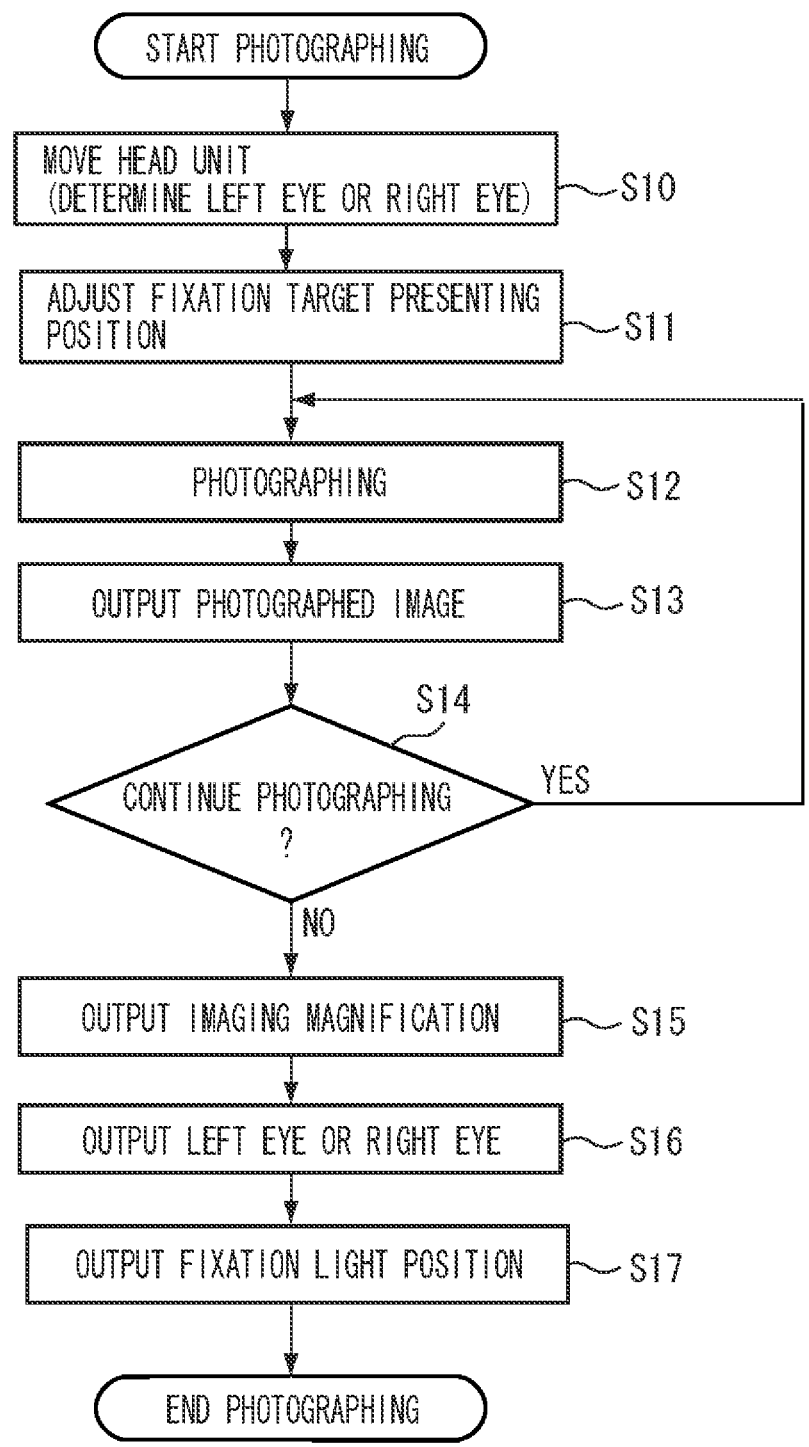
FIG. 4 illustrates a flowchart of a procedure for photographing a plurality of FAF images.

FIG. 4 illustrates a flowchart of a procedure for adjusting a position of a subject's eye and photographing a plurality of FAF images. A photographer sits a subject in front of the stage unit 20, and determines which eyes of a left eye and a right eye is photographed. Then, in step S10, the photographer operates the operation lever 21, and moves the head unit 10 toward an eye to be photographed.

In step S11, the photographer operates the fixation light operation switch 22 of the stage unit 20, and adjusts a projection position of the fixation light 16 for projecting onto a fundus Er. When the LED at a position La of the fixation light 16 is lighting at a certain time and the photographer operates the upward movement switch 22a, the fixation light control unit 17 turns off the LED at the position La and turns on the LED at a position Lb. Similarly, when the photographer operates the rightward movement switch 22d, the fixation light control unit 17 turns off the LED at the position La, and turns on the LED at a position Lc. Accordingly, by alternatively lighting the LED configuring the fixation light 16, the photographer can move the presenting position of the fixation light 16 which is seen from the subject.

The photographer prompts the subject to look firmly the presenting position of the fixation light 16. The photographer can photograph an intended fundus portion by moving the macular portion of the fundus Er which includes an optic nerve to the projection position of the fixation light 16.

In the present exemplary embodiment, the fixation light 16 which is configured with LEDs arranged in the photographing optical system is described as an example. However, a light source other than LED can be used. Further, instead of the configuration to arrange LEDs in a lattice shape and light the LED alternatively, the fixation light 16 can be configured to move one light source.

In step S12, the photographer adjust a position and focus of the fundus Er, and perform photographing of the fundus Er by operating the photographing switch 23. When the photographer operates the photographing switch 23, the fixation light control unit 17 retreats the flip-up mirror 14 from a photographing optical path, and operates so that light reflected from the fundus Er forms an image on the image sensor 15.

In steps S13, the fundus image formed on the image sensor 15 is output to and stored in the image storage unit 32 together with an imaging plane effective size and the number of image pixels of the image sensor 15.

Since an extremely weak fluorescence is captured in the photographing of the FAF image, it is difficult to obtain an image with a quality which can be used in diagnosis by only one photographing. Therefore, in step S14, the photographer determines to continue the photographing or not. When the photographer continues the photographing of the FAF image (YES in step S14), the photographer operates the photographing switch 23 and continues the photographing of the FAF image which starts from step S12. On the other hand, when the photographer ends the photographing of the FAF image (NO in step S14), the photographer operates an ending switch (not illustrated) and shifts to photographing end processing which starts from step S15.

In step S15, when the photographing is ended, the imaging magnification output unit 24 outputs the imaging magnification of the photographing optical system. Then, in step S16, the left eye and right eye detection unit 26 detects whether the subject's eye E is the left eye or the right eye from a position relationship between the stage unit 20 and the head unit 10, and outputs the detection result. In step S17, the fixation target presenting position detection unit 25 detects and outputs the presenting position of the fixation light 16 based on the control state of the fixation light control unit 17, and ends the photographing.

Figure 5:
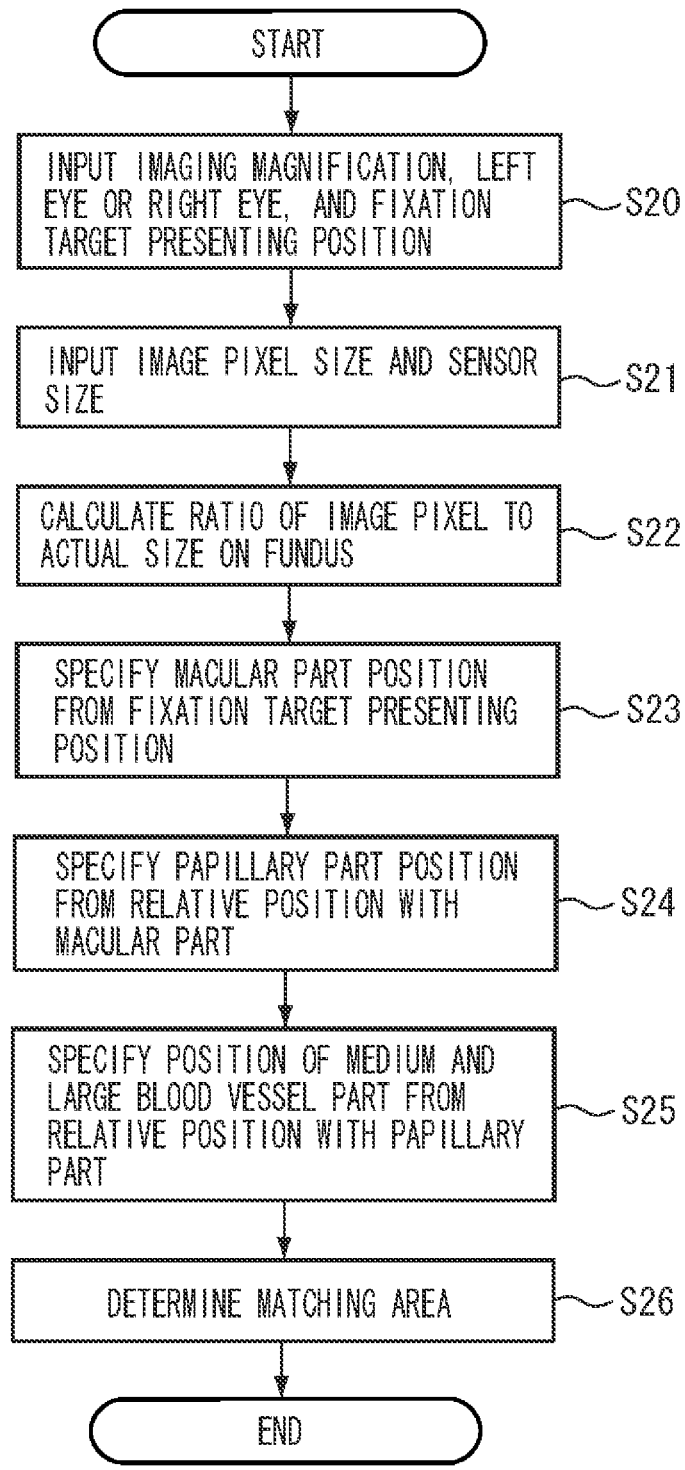
FIG. 5 illustrates a flowchart of a procedure for determining a matching area.

FIG. 5 illustrates a flowchart of a procedure for determining a matching area used for combining a plurality of photographed FAF images.

In step S20, the fundus position detection unit 31 receives outputs from the imaging magnification output unit 24, the fixation target presenting position detection unit 25, and the left eye and right eye detection unit 26, and acquires the imaging magnification at the time of fundus photographing, the fixation target presenting position, and information about a left eye and a right eye.

In step S21, the fundus position detection unit 31 reads the imaging plane effective size and the number of image pixels which are stored in the image storage unit 32, and calculates a pixel distance indicating whether a unit length on the image sensor 15 is equivalent to what numbers of pixels on the photographed image.

In step S22, the fundus position detection unit 31 calculates a fundus pixel ratio by multiplying the pixel distance calculated in step S21 by the imaging magnification acquired in step S20. The fundus pixel ratio indicates whether a unit length on the fundus Er is equivalent to what numbers of pixels on the captured image. Further, from the fundus pixel ratio calculated in step S22 and the fixation target presenting position acquired in step S20, the fundus position detection unit 31 converts the fixation target presenting position to a pixel coordinate system on the photographed image.

Figure 6:
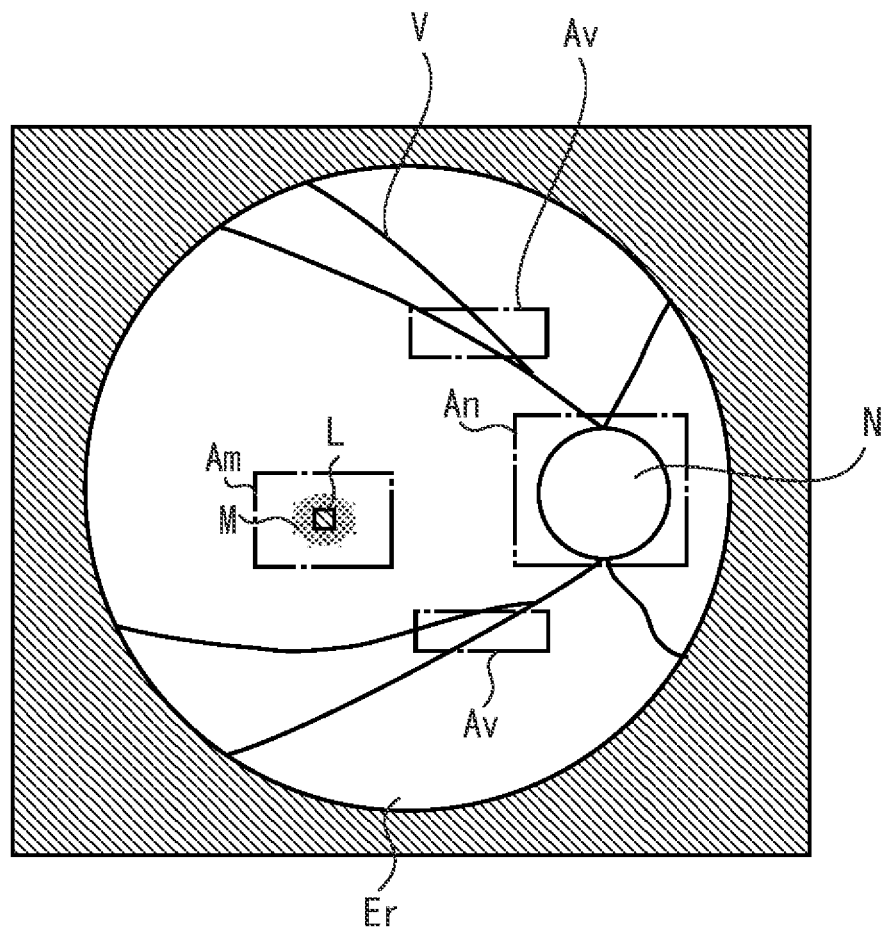
FIG. 6 illustrates a photographed image and a matching area.

As described above, the photographer performs photographing while making the subject to look firmly the fixation target presenting position. A center of the view of humans is a portion referred to as a central fovea existing at a center of a macular portion. When the subject looks firmly the fixation target presenting position, a macular portion M exists at a position overlapped with a fixation target presenting position L as illustrated in FIG. 6.

Therefore, in step S23, the conversion of the fixation target presenting position L to the pixel coordinate system is equivalent to specifying the position of the macular portion M on the photographed image of the fundus Er. By specifying the position of the macular portion M on the photographed image, a position of an optic papillary portion N can be specified.

Generally, the position relationship between the macular portion M and the optic papillary portion N on the fundus Er includes little individual difference. More specifically, as illustrated in FIG. 6, in a right eye, the optic papillary portion N is located at a position about 4 mm rightward and about 1 mm upward seeing from the macular portion M. In a left eye, the optic papillary portion N is located at a position about 4 mm leftward and about 1 mm upward seeing from the macular portion M. Therefore, in step S24, the fundus position detection unit 31 can specify the position of the optic papillary portion N on the photographed image by adding a value calculated by multiplying the fundus pixel ratio and the position relationship by the position of the macular portion M acquired in step S23.

Similarly, medium and large blood vessel portions V which extend from the optic papillary portion N are located at positions about 2 mm upward and downward from the optic papillary portion N and about 1 mm in the direction of the macular portion M. Therefore, in step S25, the fundus position detection unit 31 can also specify the position of the medium and large blood vessel portion V on the photographed image by adding a value calculated by multiplying the fundus pixel ratio and the positional relationship by the position of the optic papillary portion N acquired in step S24.

According to the above described procedure, the fundus position detection unit 31 can specify the pixel coordinates of the macular portion M, the optic papillary portion N, and the medium and large blood vessel portion V on the photographed image. The fundus position detection unit 31 outputs the specified positions of each portion to the matching area determination unit 33.

In step S26, based on generally known sizes of the macular portion M, the optic papillary portion N, and the medium and large blood vessel portion V, and the positions of each part input from the fundus position determination unit 31, the matching area determination unit 33 acquires, as a pixel unit, areas having a size which can sufficiently include the macular portion M, the optic papillary portion N, and the medium and large blood vessel portion V. Finally, the matching area determination unit 33 determines the acquired areas as a macular portion matching area Am, an optic papillary portion matching area An, and a medium and large blood vessel portion matching area Av.

Figure 7:
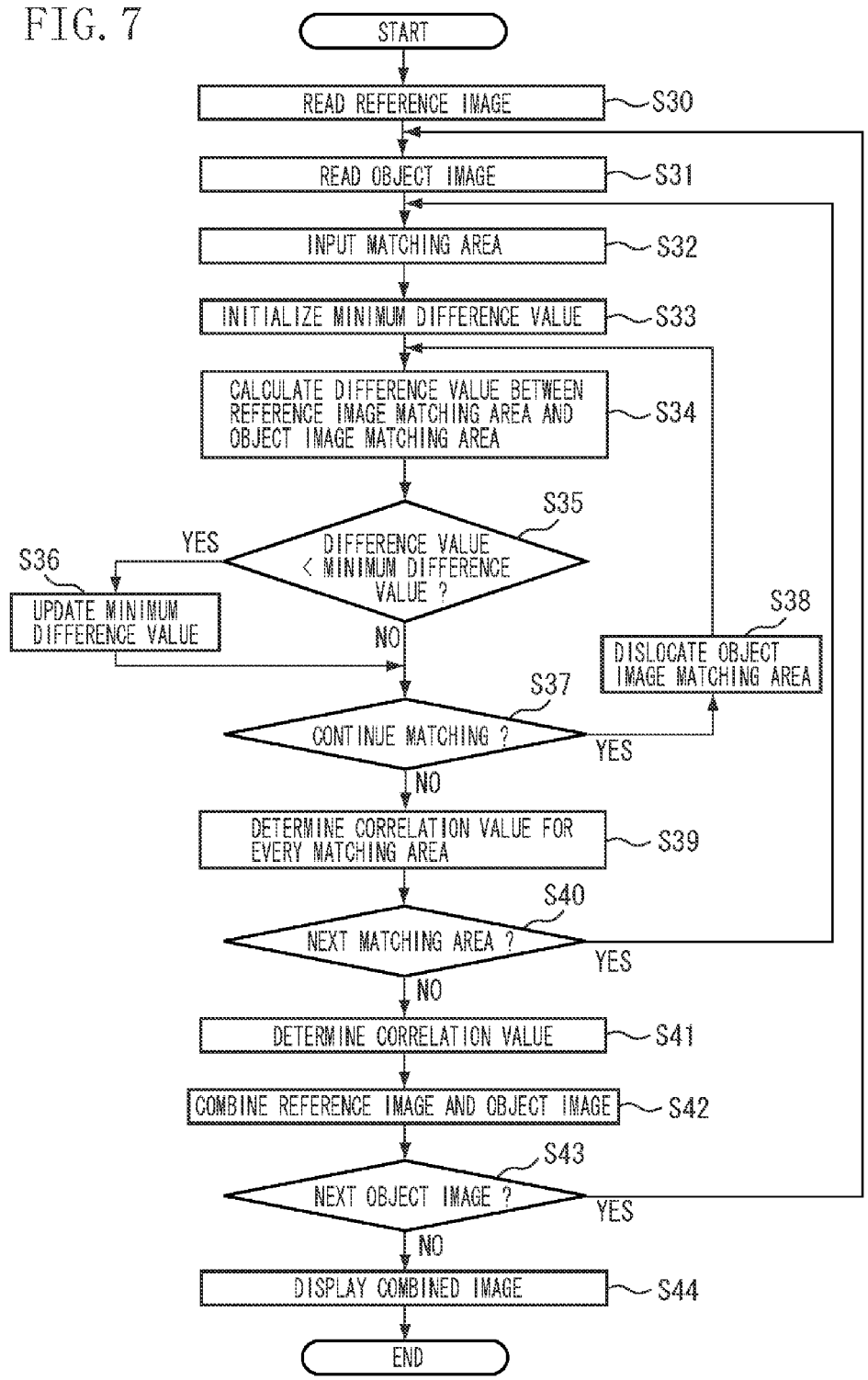
FIG. 7 illustrates a flowchart of a procedure for performing addition combination of a plurality of FAF images.

FIG. 7 illustrates a flowchart of a procedure for combining a plurality of photographed FAF images using the matching areas determined in step S26 and displaying the combined image.

In step S30, the correlation value calculation unit 35 reads one image among the plurality of the FAF images stored in the image storage unit 32, and sets the read image as a reference image.

In step S31, the correlation value calculation unit 35 reads next one image among the plurality of the FAF images stored in the image storage unit 32, and set the read image as a matching object image.

In step S32, the correlation value calculation unit 35 acquires one of the matching areas determined by the matching area determination unit 33, and starts matching processing based on the acquired matching area.

In step S33, prior to calculation of a correlation value, the correlation value calculation unit 35 initializes a storage area for storing a minimum difference value between the reference image and the matching object image, and performs initialization with a value indicating that the minimum difference value is the maximum in the initialization processing. At the same time, the correlation value calculation unit 35 initializes a storage area for storing a correlation value of the reference image and the matching area set in the matching object image. In the initialization processing, the correlation value calculation unit 35 performs the initialization with a value indicating having no horizontal deviation, no vertical deviation, rotational deviation of 0 degree, and no magnification difference.

In step S34, the correlation value calculation unit 35 reads a portion corresponding to the matching area from both the reference image and the matching object image, and calculates an image difference value of the both matching areas of the reference image and the matching object image. A general method for calculating the image difference value includes steps of acquiring pixel values which have the same coordinates from both matching areas, requiring an absolute value of difference of the pixel values, and summing the acquired absolute value of difference in the entire matching area as the image difference value. However, a square value of difference of the pixel values can be used instead of the absolute value of difference of the pixel values. Further, the other method can be used for calculating the image difference value.

In step S35, the correlation value calculation unit 35 compares the image difference value calculated in step S34 with the minimum difference value stored. When the correlation value calculation unit 35 determines that the image difference value is smaller than the minimum difference value (YES in step S35), the processing proceeds to step S36. In step S36, the correlation value calculation unit 35 overwrites the stored minimum difference value with the image difference value. At the same time, the correlation value calculation unit 35 overwrites the stored correlation values with the horizontal deviation amount, the vertical deviation amount, the rotational deviation amount, and the magnification difference between the matching area set in the reference image and the matching area set in the matching object image.

On the other hand, when the correlation value calculation unit 35 determines that the image difference value is larger than the minimum difference value (NO in step S35), then in step S37, the correlation value calculation unit 35 proceeds processing to matching end determination processing. The correlation value calculation unit 35 calculates the image difference value between the reference image and the matching object image, while displacing the matching area of the matching object image in the horizontal direction, the vertical direction, the rotational direction, the enlarging direction, and the reducing direction at a fixed width in a predetermined range.

When the matching processing in the predetermined range is not completely ended (YES in step S37), then in step S38, the correlation value calculation unit 35 displaces the matching area of the matching object image at the fixed width, and then continues the matching processing starting from step S34. On the other hand, when the matching processing in the predetermined range is completely ended (NO in step S37), the in step S39, the correlation value calculation unit 35 determines the correlation value stored at the time of ending the matching processing as a correlation value in a current matching area.

Figure 8:
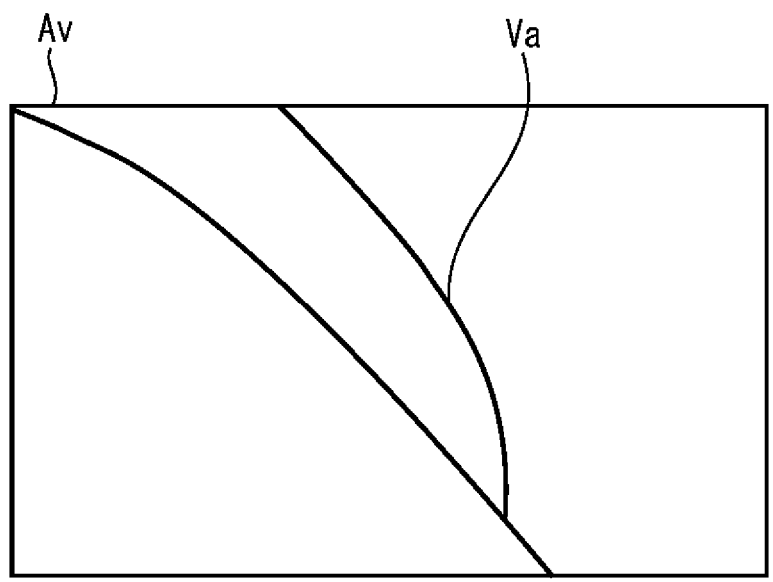
FIG. 8 illustrates a matching area in a reference image.
Figure 9:
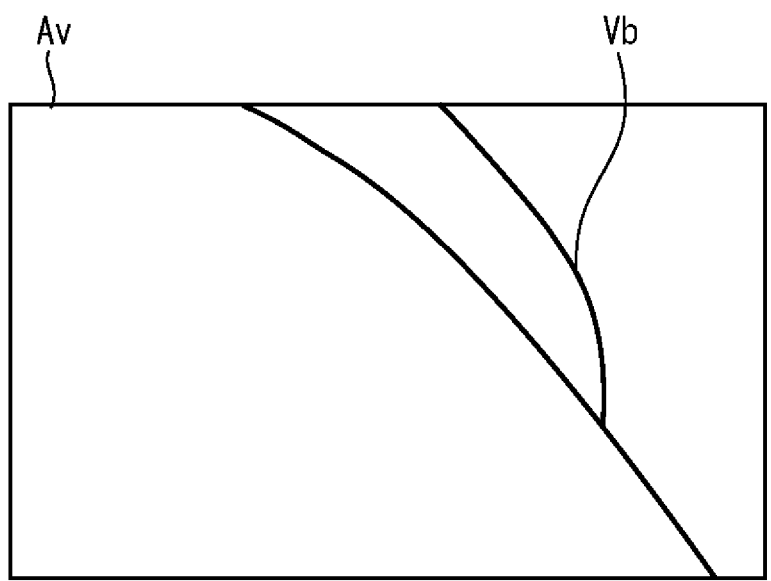
FIG. 9 illustrates a matching area in a matching object image.

FIGS. 8 to 11 illustrate the matching processing. FIG. 8 illustrates a matching area including the medium and large blood vessel portion Va of the reference image. FIG. 9 illustrates an initial matching area including the medium and large blood vessel portion Vb of the matching object image. Since fixation of a subject slightly deviates when the matching object image is photographed, the matching area of the reference image illustrated in FIG. 8 and the initial matching area of the matching object image illustrated in FIG. 9 deviate mutually.

Figure 10:
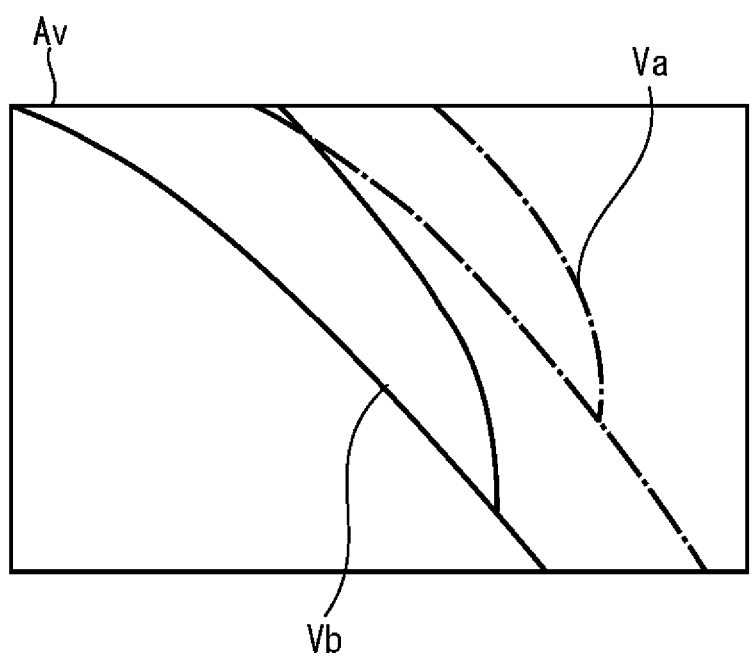
FIG. 10 illustrates difference between a reference image and a matching object image before adjusting a position.

When the correlation value calculation unit 35 calculates the image difference value in a state that the matching area of the reference image and the initial matching area of the matching object image deviate mutually, a large difference value between the medium and large blood vessel portions Va and Vb is detected as illustrated in FIG. 10. Thus, the correlation value calculation unit 35 does not determine the correlation value in this state.

Figure 11:
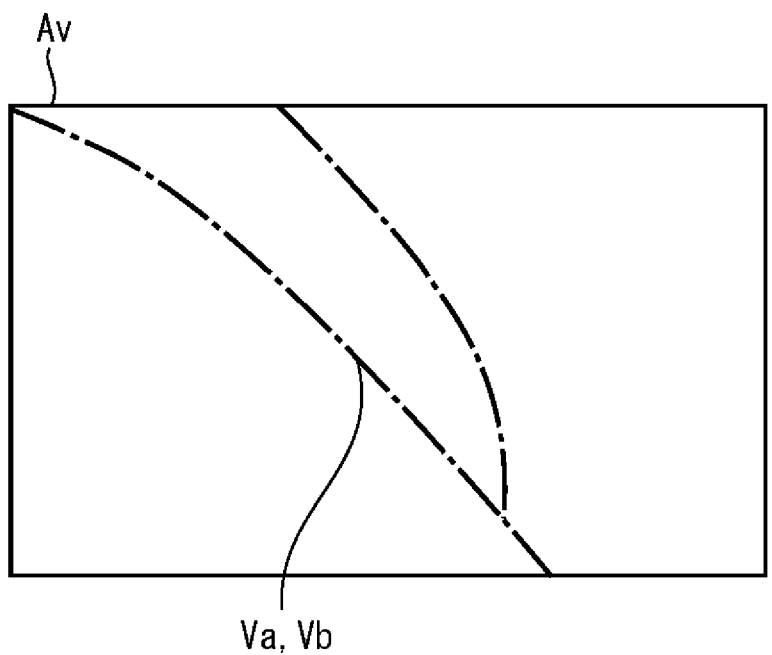
FIG. 11 illustrates difference between a reference image and a matching object image after adjusting a position.

When the correlation value calculation unit 35 repeats the matching processing by displacing the matching area of the matching object image to rightward and upward, the correlation value calculation unit 35 can make a state illustrated in FIG. 11. When the correlation value calculation unit 35 calculates the image difference value in the state in FIG. 11, the medium and large blood vessel portions Va and Vb act to cancel mutual pixel values, so that a very small difference value can be detected.

Hereafter, if the correlation value calculation unit 35 does not detect the image difference value which is further smaller than the above described very small difference value in a movement amount, a rotation amount, an enlargement amount, and a reduction amount in the matching area of the matching object image, the correlation value calculation unit 35 finally determines an amount of rightward movement and an amount of upward movement as correlation values in the state as illustrated in FIG. 11. By the procedure so far, calculation of the correlation value in one matching area is completed.

In step S40, when the matching area determination unit 33 determines a plurality of matching areas, it is determined that there is a next matching area. When there is the next matching area (YES in step S40), the similar processing starting from step S32 is repeated until the correlation value calculation unit 35 determines correlation values of the entire matching areas.

When the correlation value calculation unit 35 determines the correlation values in the entire matching areas in the procedure (NO in step S40), then in step S41, the correlation value calculation unit 35 calculates a final correlation value between the reference image and the matching object image, that is, an amount of deviation between the two images, and outputs the calculated amount of deviation to the image combining unit 34.

In the present exemplary embodiment, the correlation value calculation unit 35 calculates the correlation values respectively for every matching area. However, the correlation value calculation unit 35 can determine an average value of the correlation values as the final correlation value, and can determine a center value or the most frequently value as the final correlation value. In step S42, based on the correlation value output in step S41, the image combining unit 34 displaces the entire matching object image in the horizontal direction, the vertical direction, the rotational direction, the enlarging direction, and the reducing direction, and performs addition combining with the reference image.

In step S43, when the image storage area stores three or more FAF images, it is determined that there is a next object image. When there is the next object image (YES in step S43), the similar processing starting from step S31 is repeated until calculation of correlation values and addition combining of the FAF image with the reference image is completed for all of the FAF images. When calculation of correlation values and addition combining of all the photographed FAF images are completed (NO in step S43), then in step S44, the image combining unit 34 displays combined images on the image display unit 36.

As described above, the fundus photographing apparatus according to the present exemplary embodiment can specify a fundus position based on photographing conditions at time of fundus photographing, and can determine a matching area proper for matching between images. Therefore, the fundus photographing apparatus can determine a characteristic portion on the fundus Er of an image as a matching area even when the image includes a lot of noise components, such as a FAF image, and can correct a position deviation with high speed and high precision.

In the present exemplary embodiment, the matching area is configured to include the macular portion M, the optic papillary portion N, and the medium and large blood vessel portion V. This is because the macular portion M, the optic papillary portion N, and the medium and large blood vessel portion V include particularly many characteristic components, such as a high frequency component, in the fundus Er. Further, these portions have characteristic shapes which have large difference of luminance with peripheral portions and are appropriate for matching. However, the matching area can be configured to include portions other than the macular portion M, the optic papillary portion N, and the medium and large blood vessel portion V.

Further, in the exemplary embodiment, the fundus photographing apparatus is configured to perform addition combining of FAF images. However, the apparatus can be applied to all applications for adjusting positions of a plurality of photographed fundus images, such as for adjusting a position of stereo photographing, and for specifying a sticking position of panoramic photographing.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-124349 filed May 22, 2009, which is hereby incorporated by reference herein in its entirety.

What is claimed is:

1. A fundus photographing apparatus comprising:
    an imaging unit configured to capture a fundus image of a subject's eye via a photographing optical system;
    wherein the photographing optical system is configured to:
        capture a first fundus image of the subject's eye at a first point in time; and
        capture a second fundus image of the subject's eye at a second point in time different from the first point in time;
    a matching area determination unit configured to:
        obtain a position of a first matching area from the first fundus image; and
        search in a specific area relative to the first matching area to obtain a position of a third matching area from the first fundus image;
        obtain a position of a second matching area from a second fundus image;
        search in a specific area relative to the second matching area to obtain a position of a fourth matching area from the second fundus image;
    a correlation value calculation unit configured to:
        calculate a first correlation values between the first fundus image and the second fundus image captured by the imaging unit based on the position of the first matching area and the position of the second matching area;
        calculate a second correlation values between the first fundus image and the second fundus image captured by the imaging unit based on the position of the third matching area and the position of the fourth matching area; and
        determine a final correlation value based on the first correlation value and the second correlation value; and
    an image generation unit configured to add the first fundus image and the second fundus image based on the final correlation value.

2. The fundus photographing apparatus according to claim 1, wherein the matching area determination unit determines an area for matching by specifying an optic papillary portion, a macular portion, or a medium and large blood vessel portion of a fundus based on the imaging magnification and a presenting position of a fixation target.

3. The fundus photographing apparatus according to claim 1, wherein the matching area determination unit determines an area including an optic papillary portion or a medium and large blood vessel portion of a fundus.

4. The fundus photographing apparatus according to claim 1, wherein the correlation value calculation unit outputs an average value, a center value, or the most frequent value of the plurality of the calculated correlation values, as a correlation value.

5. The fundus photographing apparatus according to claim 1, wherein a fixation target is not moved between the first point in time and the second point in time.

6. The fundus photographing apparatus according to claim 1, wherein the optical path within the optical apparatus used in the capture of the first fundus image is identical to the optical path within the optical apparatus used in the capture of the second fundus image.

7. The fundus photographing apparatus according to claim 1, wherein:
    the photographing optical system is used to capture additional fundus images;
    the matching area determination unit obtains additional matching areas in the additional fundus images;
    the image generation unit adds the additional fundus images to the first fundus image and second fundus image so that the additional matching areas are coincident with the first matching area and the second matching area.

8. The fundus photographing apparatus according to claim 1, wherein the positions of the matching areas are relative to a fixation target presenting position.

9. The fundus photographing apparatus according to claim 1, wherein the matching areas overlap a fixation target presenting position.

10. The fundus photographing apparatus according to claim 1,
    wherein the first matching area overlaps a fixation target presenting position; and
    wherein the second matching area overlaps the fixation target presenting position.

11. The fundus photographing apparatus according to claim 1, wherein:
    the first and second plurality of correlation values are at least one of an amount of movement in a horizontal direction, an amount of movement in a vertical direction, an amount of rotation in a rotational direction, and an amount of enlargement in an enlarging direction.

12. The fundus photographing apparatus according to claim 1 wherein:
    the first matching area includes a macular portion in the first fundus image;
    the third matching area includes an optic papillary portion in the first fundus image;
    the second matching area includes the macular portion in the second fundus image; and the fourth matching area includes the optic papillary portion in the second fundus image.

13. The fundus photographing apparatus according to claim 1 wherein:
the first matching area includes a macular portion in the first fundus image;
the third matching area includes an intersection of a first blood vessel and a second blood vessel in the first fundus image;
the second matching area includes the macular portion in the second fundus image; and
the fourth matching area includes the intersection of the first blood vessel and the second blood vessel in the first fundus image in the second fundus image.

14. A method comprising:
capturing a first fundus image of the subject's eye at a first point in time; and
capturing a second fundus image of the subject's eye at a second point in time different from the first point in time;
obtaining a position of a first matching area from the first fundus image; and
searching in a specific area relative to the first matching area to obtain a position of a third matching area from the first fundus image;
obtaining a position of a second matching area from a second fundus image; and
search in a specific area relative to the second matching area to obtain a position of a fourth matching area from the second fundus image;
calculating a first correlation values between the first fundus image and the second fundus image based on the position of the first matching area and the position of the second matching area;
calculating a second correlation values between the first fundus image and the second fundus image based on the position of the third matching area and the position of the fourth matching area; and
determining a final correlation value based on the first correlation value and the second correlation values; and
adding the first fundus image and the second fundus image based on the final correlation value.

15. The fundus photographing apparatus according to claim 1, further comprising:
a fixation target presenting unit configured to make the subject's eye to look firmly at a fixation target.

16. The fundus photographing apparatus according to claim 1, wherein:
the first and second correlation values include an amount of rotation in a rotational direction.

17. The fundus photographing apparatus according to claim 1, wherein:
the first and second correlation values include an amount of enlargement in an enlarging direction.

18. A fundus photographing apparatus comprising:
an imaging unit configured to capture a fundus image of a subject's eye via a photographing optical system;
wherein the photographing optical system is configured to:
capture a first fundus image of the subject's eye at a first point in time; and
capture a second fundus image of the subject's eye at a second point in time different from the first point in time;
a matching area determination unit configured to:
obtain a position of a first matching area from the first fundus image based on a position of a fixation target in the first fundus image which is obtained based on a fixation target presenting position; and
obtain a position of a second matching area from a second fundus image based on a position of a fixation target in the second fundus image which is obtained based on the fixation target presenting position; and
an image generation unit configured to add the first fundus image and the second fundus image based on a correlation between the first matching area and the second matching area.

19. A method comprising:
capturing a fundus image of a subject's eye via a photographing optical system;
capturing a first fundus image of the subject's eye at a first point in time; and
capturing a second fundus image of the subject's eye at a second point in time different from the first point in time;
obtaining a position of a first matching area from the first fundus image based on a position of a fixation target in the first fundus image which is obtained based on a fixation target presenting position; and
obtaining a position of a second matching area from a second fundus image based on a position of a fixation target in the second fundus image which is obtained based on the fixation target presenting position; and
adding the first fundus image and the second fundus image based on a correlation between the first matching area and the second matching area.

* * * * *